United States Patent [19]

Michael

[11] Patent Number: 4,786,604

[45] Date of Patent: Nov. 22, 1988

[54] LEAD DETECTOR KIT

[76] Inventor: Robert C. Michael, 426 N. Jackson St., Apt. 203, Glendale, Calif. 91206

[21] Appl. No.: 65,356

[22] Filed: Jun. 22, 1987

[51] Int. Cl.⁴ ..................... G01N 33/20; G01N 31/22
[52] U.S. Cl. ......................................... 436/77; 422/61
[58] Field of Search ....................... 422/61, 58, 68.08; 436/182, 164, 165, 74, 77

[56] References Cited

U.S. PATENT DOCUMENTS 3,809,537  5/1974  Horine .
4,125,376  11/1978  Razulis .

FOREIGN PATENT DOCUMENTS 0120250  6/1985  Japan ................................. 436/164

OTHER PUBLICATIONS

Chemical Abstracts 89(8):70217n.

*Primary Examiner*—Barry S. Richman
*Assistant Examiner*—Lyle Alfandary-Alexander
*Attorney, Agent, or Firm*—James E. Brunton

[57] ABSTRACT

A method and apparatus for detecting the existence of lead in tapwater. The apparatus comprises a kit having one vial filled with a reference solution exhibiting the appearance of clear, partially diluted sodium chromate. A second vial is partially filled with a saturated sodium or potassium chromate solution. Testing is accomplished by filling the second vial with the tap water, permitting any lead within the tap water to react with the sodium or potassium chromate and then visually comparing the resulting clarity of the test solution and the reference solution.

9 Claims, 1 Drawing Sheet

LEAD DETECTOR KIT

BACKGROUND OF THE INVENTION

1. Field of the Invention

The present invention relates generally to an improved method and apparatus for detecting the existence of lead in a domestic water supply. More particularly, the invention concerns an apparatus in kit form which can be used by untrained members of the public in their own homes to test for excessive concentrations of lead in their tap water.

2. Discussion of the Prior Art

The contamination of domestic drinking water by dissolved lead is a source of great concern in the United States and other parts of the world. Although the deleterious health effects of ingested lead have been known for centuries, lead piping is commonplace in older residences, particularly those located in the eastern United States. While most newer homes now have galvanized steel, PVC plastic or copper plumbing, until very recently the copper was joined by use of lead-tin alloy solder. While solder of this composition is now being phased out, millions of newer homes still have lead-soldered plumbing.

Lead occurs in the drinking water primarily as a corrosion by-product of the materials used in residential plumbing systems. Water leaving the water treatment plant is typically relatively lead-free. However, pipes and solder containing lead are readily corroded by water, especially soft and acidic water and lead levels at the domestic user's tap can be much higher than those found at the treatment plant. Of substantial concern is the combination of copper pipes with solder containing lead now found in many households which can result in high lead levels, particularly in first-drawn water that has been in contact with the pipe for a period of time. It is now well recognized that newly-installed solder is easily dissolved, and people living in new housing, or in older housing but with new plumbing, wherein copper connections have been made with lead-tin alloy solder, are especially at risk of high levels of lead in the drinking water.

Because of the serious problems presented by lead contaminated drinking water, a method by which the average homeowner can simply and inexpensively test tap water to qualitatively determine if a high level of dissolved lead is present is desperately needed. The invention described herein fills this need by providing a simple, rapid and lead-specific test for aqueous lead in concentrations down to about five parts per million. Additionally, the detection method of the invention will not give an indicator precipitate with other common metallic ionic species in tap water, such as iron, zinc, copper, calcium and magnesium.

One well-known qualitative test for lead together with certain other metals such as copper, bismuth, and antimony consists of adjusting the pH to the region of about 0 to 2 and bubbling in hydrogen sulfide gas. If lead is present in sufficient quantity, a black precipitate (lead sulfide) is formed.

It is also known that amounts of lead on the order of four to seven parts per million can be determined by using dithizone or various instrumental methods. However, such tests require special equipment and chemicals, and often involve complicated experimental procedures. This type of test cannot easily be conducted by average persons in their own home.

Another technique for testing lead leached from pottery is disclosed in U.S. Pat. No. 3,809,537 issued to Angela A. Horine. This test involves extracting lead from the suspect pottery in an acid medium and reacting the resulting solution with an aqueous solution of sodium sulfide to produce an indicator precipitate of lead sulfide.

U.S. Pat. No. 4,125,376, issued to Razulis, discloses a test for various organic and inorganic water contaminants using a test tube with a small cube of synthetic sponge which is saturated with an indicator compound. For inorganic metal salts, the foam cube is impregnated with a solution of dithizone. A change in color of the cube indicates the presence of the salts of various heavy metals such as chromium, cobalt, lead, mercury and zinc in the water being tested. Lead chromate, thiocyanate, and sulfate were detected by a change in color of the cube from bright green to pinkish gray at a limit of 200 micrograms/liter.

None of the previously identified testing techniques are well suited for use by laymen in testing concentrations of lead in tap water.

SUMMARY OF THE INVENTION

It is an object of the present invention to provide a simple test for detection of detrimental concentrations of lead in the domestic water supply which can readily be accomplished by untrained members of the public in their own homes.

Another object of the invention is to provide a testing apparatus in kit form which can be readily purchased by the public, as for example from supermarkets and drug stores, and used in the home without the necessity of mixing any type of potentially dangerous chemicals.

Still another object of the invention is to provide an apparatus of the above-mentioned character which is safe to transport and use.

Yet another object of the invention is to provide a testing kit which is compact, easy to package, and inexpensive to produce.

DESCRIPTION OF THE INVENTION

Figure 1:
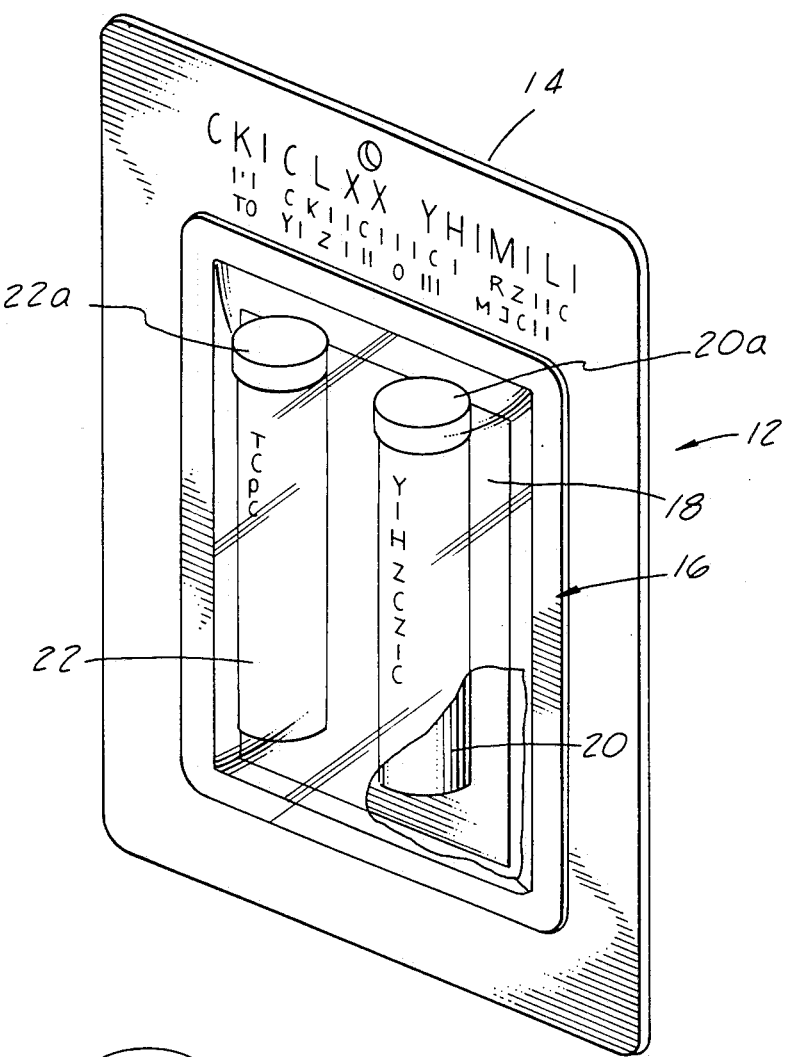
FIG. 1 is a generally perspective view of the lead detection kit of the present invention.

Referring to the drawings, the apparatus, or kit, for testing for lead concentrations in water in excess of five parts per million is generally designated by the numeral 12. As indicated in FIG. 1, the apparatus of this form of the invention comprises a display and transport package including a substantially planar backing member 14 and a vial enclosing means generally designated by the numeral 16. Backing member 14 may be constructed of any suitable rigid material such as cardboard, sheet plastic or the like. In the embodiment of the invention shown in FIG. 1, the vial enclosing means comprises a substantially transparent, thin film plastic envelope 18 which is affixed proximate its outer margins to backing member 14 by any suitable means such as heat welding or gluing.

Figure 2:
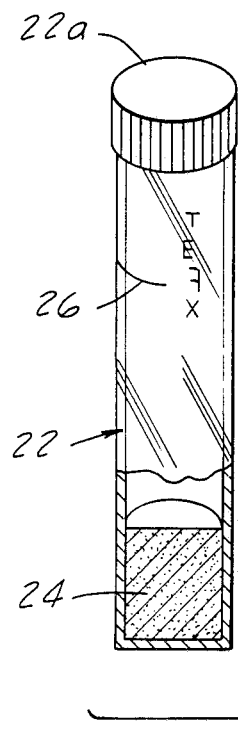
FIG. 2 is a generally perspective view of the substantially transparent vials shown in FIG. 1 with the vial at the left containing a testing solution to which the water to be tested is added and with the vial to the right containing a reference, or comparison, solution.
Figure 2:
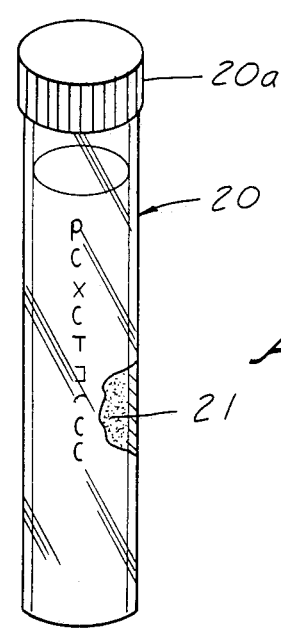

Contained within the vial enclosing means is a first vial 20, preferably having a volume of about four milliliters and being constructed from a substantially transparent material such as glass or a suitable plastic material. Vial 20 is closely contained within the vial enclosing means and held in position against the backing member in the manner shown in FIG. 1. Vial 20 is closed by a tight fitting cap 20a. Contained within vial 20 is a reference solution having the appearance of clear sodium or potassium chromate solution. The reference solution may be prepared in a variety of ways using a yellow dye mixed with a suitable liquid medium. While various dyes and liquid mediums can be used to prepare the reference solution, a mixture of yellow food coloring and water has proven satisfactory as a way of closely duplicating the appearance of a clear somewhat dilute sodium or potassium chromate solution. As indicated in FIG. 2, vial 20 is substantially filled with the reference solution 21.

Also enclosed within the vial enclosing means is a second four milliliter vial 22 which is also constructed of a substantially transparent material. The second vial is carried within the enclosing means alongside the first vial and is partially filled with a test solution comprising a saturated sodium or potassium chromate solution in distilled water designated in FIG. 2 by the numeral 24. A line 26 is scribed in vial 22 at a location generally corresponding to the top of the reference solution contained in vial 20. Vial 22 is also closed by a tight fitting cap 22a.

The method of the present invention for testing for lead concentrations in water in excess of approximately five parts per million comprises the following steps: First, a reference solution is mixed in four milliliter vial 20 in a manner so that the solution has the appearance of a diluted, clear sodium or potassium chromate solution. More particularly, the reference solution is prepared using a yellow dye and a suitable liquid medium to closely duplicate the appearance of a saturated sodium or potassium chromate solution which has been diluted with distilled water of approximately equal volume to the saturated solution. While various dyes and liquid mediums may be used in preparing the reference solution, yellow food dye mixed with water has been found to provide a simple and inexpensive way to closely duplicate the appearance of the diluted sodium or potassium chromate solution.

Next, within second substantially transparent, four milliliter vial 22, a saturated sodium or potassium chromate solution is prepared. Preferably, vial 22 is approximately half filled with the testing solution, that is, with about two milliliters of a saturated sodium or potassium chromate solution which has been prepared using powdered sodium or potassium chromate and distilled water in suitable proportions to obtain a fully saturated solution.

After preparation of the reference and test solutions, the tap water, or other water sample, is tested for lead contamination in the following manner. First, about two milliliters of the water to be tested are added to the second vial containing the test solution. This should fill the second vial to about the level of scribe line 26. Cap 22a is then firmly placed on the second vial and the vial is briskly shaken to thoroughly mix the water to be tested with the saturated sodium or potassium chromate solution. Next, the mixture of tap water and sodium or potassium chromate is allowed to stand undisturbed within upright second vial 22 for on the order of thirty minutes. This allows the indicator reaction to fully take place and for any air bubbles formed during the mixing step to dissipate. The reaction which takes place is:

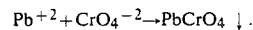

$$Pb^{+2} + CrO_4^{-2} \rightarrow PbCrO_4 \downarrow .$$

After the expiration of about thirty minutes, the reference vial containing the premixed reference solution is placed alongside the second vial containing the mixture of the test water and the sodium or potassium chromate and both vials are held up to a light source. If the solution in the first and second vials appears to have approximately the same clarity, then any lead which may have been contained within the test sample can be concluded to have been less than approximately five parts per million. On the other hand, if the solution contained within the second vial has a cloudy appearance when compared with the clear reference solution, then it can be concluded that the water which was added to the second vial contains in excess of approximately five parts per million lead.

When the test kit is packaged in the manner shown in FIG. 1, the first vial 20 already contains the appropriately mixed test solution 21. Similarly, the second vial 22 contains about two milliliters of saturated sodium or potassium chromate. All the purchaser of the kit need do to accomplish a test of the tap water is to first add approximately two milliliters of tap water to second vial 22 so that the water level reaches the height of the scribe line 26. Next, cap 22a is affixed and the vial shaken briskly. Following thorough mixing of the test solution and the tap water, vial 22 is allowed to stand for about thirty minutes to allow the tap water to react with the test solution. Finally, the first and second vials are held up to a bright light, or to sunlight, so that the relative clarity of the test solution and the reference solution can be compared. Comparable clarity of the solutions indicates the absence of elevated levels of lead in the water. Perceptable cloudiness of the test solution as compared to the reference solution indicates levels of lead in the tap water in excess of approximately five parts per million. Water which is discolored, turbid or highly mineralized may not give valid results.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A kit for testing for lead concentrations in water in excess of approximately five parts per million comprising:
   a packaging means including;
   (a) a first vial constructed from a substantially transparent material and containing a non-chromate reference solution having the appearance of a clear sodium chromate solution, that is an optically clear yellow tinted liquid; and
   (b) a second vial constructed from a substantially transparent material, said second vial being partially filled with a test solution comprising a saturated sodium chromate solution.

2. A kit as defined in claim 1 in which said reference solution comprises a mixture of yellow dye and a liquid medium.

3. A kit as defined in claim 1 further including packaging means comprising:
   (c) a generally planar backing member;
   (d) a substantially transparent envelope affixed to said planar backing member for enclosing said first and second vials.

4. A testing kit as defined in claim 3 in which said vial enclosing means comprises a substantially transparent thin plastic sheet material affixed proximate the margins thereof to said backing member.

5. A drinking water testing kit for determining lead concentrations in excess of approximately five parts per million in domestic water supplies, comprising:
   (a) a display and transport package including:
     (i) a substantially planar backing member; and
     (ii) a vial enclosing means affixed to said backing member;
   (b) a first vial constructed from a substantially transparent material, said vial being disposed within said vial enclosing means and containing therewithin a non-chromate reference solution comprising a mixture of yellow coloring and water said solution being free of precipitate and having the appearance of a clear sodium chromate solution; and
   (c) a second vial constructed from a substantially transparent material, said second vial being disposed within said vial containing means and being partially filled with a test solution comprising a saturated sodium chromate solution.

6. A method for testing for lead concentrations in water in excess of approximately five parts per million, comprising the steps of:
   (a) mixing within a first, substantially transparent vial a yellow dye and a liquid medium to form a non-chromate reference solution having the appearance of a clear sodium chromate solution, that is an optically clear yellow tinted liquid free of precipitate;
   (b) mixing within a second substantially transparent vial a saturated sodium chromate solution;
   (c) adding the water to be tested to said second vial containing said saturated sodium chromate solution;
   (d) thoroughly mixing the water to be tested with said saturated sodium chromate solution;
   (e) placing said second vial in an upright, at rest position for a period of time sufficient to permit any lead contained in the water sample to react with the sodium chromate; and
   (f) comparing the mixture thus formed in said second vial with said reference solution to detect an appearance of greater relative cloudiness in said second vial, thereby indicating the presence of lead in said second vial in an amount in excess of approximately five parts per million.

7. A method as defined in claim 6 in which said first and second vials each have a volume of approximately four milliliters; in which said first vial is substantially filled with said reference solution; in which said second vial is filled with approximately 2 milliliters of a saturated sodium chromate solution in distilled water prior to adding the water to be tested to said second vial.

8. A method as defined in claim 7 in which said yellow dye comprises yellow food coloring and in which said liquid medium comprises water.

9. A kit for testing for lead concentrations in water in excess of approximately five parts per million comprising:
   a packaging means including;
   (a) a first vial constructed from a substantially transparent material and containing a non-chromate reference solution being free of precipitate and having the appearance of a clear potassium chromate solution; and
   (b) a second vial constructed from a substantially transparent material, said second vial being partially filled with a test solution comprising a saturated potassium chromate solution.

* * * * *